United States Patent [19]

Paciorek et al.

[11] Patent Number: 5,550,277
[45] Date of Patent: Aug. 27, 1996

[54] PERFLUOROALKYL AND PERFLUOROALKYLETHER SUBSTITUTED AROMATIC PHOSPHATES, PHOSPHONATES AND RELATED COMPOSITIONS

[76] Inventors: Kazimiera J. L. Paciorek, 1425 Seacrest Dr., Corona Del Mar, Calif. 92625; Wen-Huey Lin, 24362 Hilton Way; Steven R. Masuda, 29322 Crown Ridge, both of Laguna Niguel, Calif. 92656; James H. Nakahara, 10 Wickland, Irvine, Calif. 92720

[21] Appl. No.: 375,954

[22] Filed: Jan. 19, 1995

[51] Int. Cl.$^6$ ................ C07F 9/09; C07F 9/32; C07F 9/40
[52] U.S. Cl. ............ 558/194; 558/207; 558/211; 558/215
[58] Field of Search .................. 558/194, 207, 558/211, 215

[56] References Cited

U.S. PATENT DOCUMENTS

| | | | |
|---|---|---|---|
| 2,694,083 | 11/1954 | Moreton et al. | 558/211 X |
| 2,890,235 | 6/1959 | Raley, Jr. et al. | 558/211 |
| 3,288,890 | 11/1966 | Blake et al. | 558/215 |
| 3,346,668 | 10/1967 | Dalton et al. | 558/207 |

*Primary Examiner*—Robert W. Ramsuer
*Assistant Examiner*—Michael G. Ambrose

[57] ABSTRACT

Perfluoroalkyl and perfluoroalkylether substituted aromatic phosphates, phosphonates and related compositions prepared by reaction of pefluoroalkyl or pefluoroakylether substituted phenols with mono- and dihalophosphite and primary and secondary phosphonyl halides are disclosed. These materials are useful as antioxidant, anticorrosion, antirust, and lubricity enhancing agents for perfluoropolyalkylether fluids.

11 Claims, No Drawings

PERFLUOROALKYL AND PERFLUOROALKYLETHER SUBSTITUTED AROMATIC PHOSPHATES, PHOSPHONATES AND RELATED COMPOSITIONS

RIGHTS OF THE GOVERNMENT

The invention was made with partial Government support under contract No. F33615-90-C-5917 awarded by the U.S. Air Force. The Government has certain rights in this invention.

FIELD OF THE INVENTION

The invention relates to a series of perfluoroalkyl and perfluoroalkylether substituted aromatic phosphates and phosphonates and related compositions for use as additives in perfluoropolyalkylether fluids.

BACKGROUND OF THE INVENTION

Because of their thermal and oxidative stability and wide fluid ranges perfluoropolyalkylether fluids are being considered for use as engine oils, hydraulic fluids and greases and are actually used currently in space guidance systems and computer disc drives, among others. However, in oxidizing atmospheres and under conditions of boundary lubrications these compositions corrode metals/metal alloys and form volatile degradation products. Two kinds of additives were found to be effective in arresting the degradation process namely phospha-s-triazines described by K. L. Paciorek, R. H. Kratzer, J. Kaufman and T. I. Ito in U.S. Pat. No. 4,215,072 (1980), and by K. L. Paciorek, R. H. Kratzer, J. Kaufman and T. I. Ito in U.S. Pat. No. 4,166,071 (1979). The other type of additives are the phosphines described by C. E. Snyder, Jr. and C. Tamborski in U.S. Pat. No. 4,097,388 (1978) and C. T. Tamborski, C. E. Snyder, Jr. and J. B. Christian in U.S. Pat. No. 4,454,349 (1984). The additives disclosed in the present invention are more effective in arresting the degradation of perfluoropolyalkylether fluids in oxidizing atmospheres at elevated temperatures in the presence of metals/metal alloys than the currently used compounds. In addition these materials can function as rust inhibitors and provide lubricity enhancement. This invention pertains specifically to the synthesis of the perfluoroalkyl and perfluoroalkylether substituted aromatic phosphates, phosphonates and related compositions. These materials and the chemical intermediates employed in their preparation and disclosed herein are, to the best of our knowledge, new chemical compounds previously unknown.

SUMMARY OF THE INVENTION

It is the principal object of this invention, therefore, to provide high temperature, antioxidation/antidegradation and metal/metal alloy corrosion inhibiting additives for perfluoropolyalkylether fluids.

Another object of the invention is to provide rust inhibiting additives for perfluoropolyalkylether fluids, poly(chlorotrifluoroethylene) and other halogenated fluids.

Additional object of the invention is to provide lubricity enhancing additives for perfluoropolyalkylether fluids.

A further object of the invention is to provide the perfluoroalkyl and perfluoroalkylether substituted aromatic phosphates, phosphonates and related compositions.

Another yet object of the invention is to provide a process for synthesizing these perfluoroalkyl and perfluoroalkylether substituted aromatic phosphates, phosphonates and related compositions.

Other objects and advantages of the invention will become apparent to those skilled in the art upon consideration of the accompanying disclosure.

DESCRIPTION OF THE PREFERRED EMBODIMENTS

The present invention resides in phosphates and phosphonates and related compositions of the following general formulas:

$$(R_fC_6H_4)_xP(O)(OR)_{3-x}$$

$$(R_fC_6H_4O)_{x-y}P(O)(OR)_{3-x}(OH)_y$$

$$(R_fC_6H_4O)_xP(O)(R)_{3-x}$$

$$(R_fC_6H_4O)_{x-y}P(O)(R)_{3-x}(OH)_y$$

wherein x is an integer 1, 2 and 3, y is <1, $R_f$ is perfluoroalkyl or perfluoroalkylether group and R are aryl groups. Examples of $R_f$ substituents include groups having the formula $C_nF_{2n+1}$, wherein n is an integer from 1 to 10 inclusive and $C_3F_7(OCF(CF_3)CF_2)_m$, $CF_3(OCF_2CF_2)_m$, $C_2F_5(OCF_2CF_2)_m$, $C_3F_7(OCF_2CF_2CF_2)_m$ or $C_4F_9(OCF_2CF_2CF_2CF_2)_m$ where m is an integer from 1 to 20 inclusive, preferably an integer from 1 to 10 inclusive. Examples of R groups include $C_6H_5$, $R'$—$C_6H_4$, where R' is an aromatic, alkyl, thioaryl ($SC_6H_5$) or a phenoxy ($OC_6H_5$) group. In one embodiment, the present invention resides in a process of preparing the phenol intermediates:

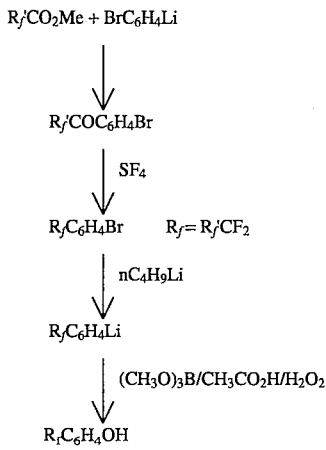

The preparation of $R_fC_6H_4Br$ wherein $R_f$ include the following $C_3F_7(OCF(CF_3)$—$CF_2)x$ and $C_2F_5(OCF_2CF_2)_y$ has been described by C. T. Tamborski, C. E. Snyder, Jr. and J. B. Christian, U.S. Pat. No. 4,454,349 (1984). The subsequent reaction with n-butyl lithium is preferably carried out in ether at −5° to −20° C. over 0.5 to 3 hour period, followed by the addition of the resultant cold solution to a solution of trimethyl borate in ether preferably at −5° to −20° C. The reaction period usually ranges from 0.5 to 4 hours. The next step is the addition of acetic acid and then hydrogen peroxide, performed preferably at −5° to −20° C. After stirring at room temperature over a period ranging from 4 to 72 hours the product is isolated with ether. All the reactions with the exception of the last step are carried out under an inert gas such as nitrogen, helium or argon. All the starting materials are commercially available.

Synthesis of phosphate additives:

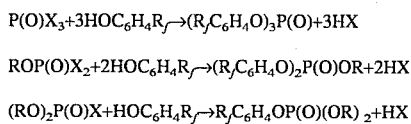

Synthesis of phosphate related additives:

P(O)X$_3$+(3-y)HOC$_6$H$_4$R$_f$→(R$_f$C$_6$H$_4$O)$_{3-y}$P(O)(OH)$_y$+(3-y)HX  y<1

ROP(O)X$_2$+(2-y)HOC$_6$H$_4$R$_f$→(R$_f$C$_6$H$_4$O)$_{2-y}$P(O)OR(OH)$_y$+(2-y)HX  y<1

Synthesis of phosphonate additives:

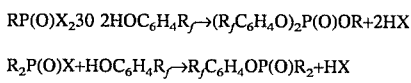

Synthesis of phosphonate related additives:

RP(O)X$_2$+(2-y)HOC$_6$H$_4$R$_f$→(R$_f$C$_6$H$_4$O)$_{2-y}$P(O)(OH)$_y$+(2-y)HX  y<1

The processes leading to the phosphates, phosphonates and the related compositions are preferably conducted in an aromatic solvent such as benzene or in a mixed aromatic/fluorinated solvent such as benzene and 1,1,2-trifluoro-1,2,2-trichloroethane or related solvent mixture in the presence of an acid acceptor such as a tertiary amine using equivalent quantities of the phenol, or somewhat lower than equivalent quantities of the phenol, and the phosphorus halide, wherein X is either chlorine or bromine. The reaction is performed preferably at 25° to 80° C. under an inert gas such as nitrogen, helium or argon. The reaction periods range from 8 to 96 hours. The halophosphorus reagents are commercially available.

EXAMPLE I

Under nitrogen bypass to n-butyllithium (55 mmol) in ether (150 mL) at −15° C. was added C$_3$F$_7$[OCF(CF$_3$)CF$_2$]$_2$C$_6$H$_4$Br (29.1 g, 44.2 mmol) over period of 30 minutes. After 2 hour stirring at −15° C. the cold solution was added, at −15° C., to a solution of trimethyl borate (20.0 g, 193 mmol) in ether (150 mL) and the resultant solution was then stirred for 31 hours at −15° C. Next, was added acetic acid (11.0 g) followed, 30 minutes later, by hydrogen peroxide (15%, 60 mL). After stirring overnight the product was isolated in ether, washed with acidic ferrous sulfate solution and after solvent removal it was purified by filtration through silica gel column followed by distillation to give 18.2 g (69% yield) of C$_3$F$_7$[OCF(CF$_3$)CF$_2$]$_2$C$_6$H$_4$OH, BP 63°–65° C./0.001 mm Hg. The material was characterized by mass spectrometry. MS (70 eV) m/e (intensity, ion): 594 (7.7%, M), 574 (3.3%, M-HF), 243 (15.2%, C$_3$F$_6$C$_6$H$_4$OH), 143 (base, CF$_2$C$_6$H$_4$OH).

EXAMPLE II

A mixture of 4-iodophenol (7.3 g, 31.8 mmol), copper bronze (7.0 g, 105 mmol) and perfluorooctyl iodide (19.9 g, 35 mmol) in dimethyl formamide (70 mL) was stirred under nitrogen atmosphere at 100°–105° C. for 70 hours. The product was isolated with ether and purified by sublimation to give 11.0 g (68% yield) of C$_8$F$_{17}$C$_6$H$_4$OH, MP 74°–75° C. The material was characterized by mass spectrometry. MS (70 e/V) m/e (intensity, ion): 512 (20.2%, M), 493 (17.2% M-F), 492 (29.6%, M-HF), 143 (base, M-C$_7$F$_{15}$).

EXAMPLE III

In a nitrogen atmosphere to a stirred solution of C$_3$F$_7$[OCF(CF$_3$)CF$_2$]$_2$C$_6$OH (19.0 g, 32.0 mmol) and C$_6$H$_5$OP(O)Cl2 (3.5 g, 16.0 mmol) in Freon 113 (Du Pont trade name) (60 mL) was added triethylamine (6.6 g, 65 mmol) in benzene (40 mL). Subsequently, the mixture was heated at 65° C. for 20 hours. The product obtained after filtration of the triethylamine hydrochloride followed by solvent evaporation was purified by distillation to give 16.7 g (79% yield) of [C$_3$F$_7$(OCF(CF$_3$)CF$_2$)$_2$C$_6$H$_4$O]$_2$-P(O)OC$_6$H$_5$, BP 169°–170° C./0.001 mm Hg; MW 1320 (theory 1326.46). MS (70 eV) m/e (intensity, ion): 1326 (30.7%, M), 1207 (16.5%, M-C$_2$F$_5$), 1041 (15.8%, M-C$_3$F$_7$OCF(CF$_3$)), 975 (17.0%, M-C$_3$F$_7$OCF(CF$_3$)—CF$_2$O), 875 (74.9%, M-C$_3$F$_7$OCF(CF$_3$)CF$_2$OCF(CF$_3$)), 212 (46.3%, C$_2$F$_5$C$_6$H$_4$OH), 205 (15.5%, CF$_2$C$_6$H$_4$PO$_3$), 69 (base, CF$_3$). Under 4 ball test conditions using a load of 600N, and 100 rpm in air, the wear rate of 1% formulation of [C$_3$F$_7$(OCF(CF$_3$)CF$_2$)$_2$C$_6$H$_4$O]$_2$P(O)OC$_6$H$_5$ in Krytox 143AC (Du Pont trade name) was 1×10$^{-9}$±0.2×10$^{-9}$ mm/mm$^3$. The wear rate for the Krytox 143AC fluid alone was 7×10$^{-9}$ mm/mm$^3$.

EXAMPLE IV

In a nitrogen atmosphere to a stirred solution of C$_2$F$_5$C$_6$H$_4$OH (1.2 g, 5.7 mmol), POCl$_3$ (0.29 g, 1.9 mmol) in benzene (5 mL) was added triethylamine (1.1 g, 11.4 mmol) in benzene (5 mL). Subsequently, the mixture was heated at 85° C. for 18 hours. The product obtained, after filtration of the triethylamine hydrochloride, followed by solvent evaporation was purified by crystallization from benzene to give 1.1 g (87% yield) of (C$_2$F$_5$C$_6$H$_4$O)$_3$P(O), MP 89°–90° C.; MW 720 (theory 680.33). MS (70 eV) m/e (intensity, ion); 611 (77.9%, M-CF$_3$), 469 (16.4%, M-OC$_6$H$_4$C$_2$F$_5$), 450 (18.5%, M-OC$_6$H$_4$C$_2$F$_5$-F), 271 (72.2%, C$_2$F$_4$C$_6$H$_4$OP(O)$_3$), 189 (51.5%, CF$_2$C$_6$H$_4$OPO), 145 (base, CF$_3$C$_6$H$_4$).

EXAMPLE V

In a nitrogen atmosphere to a stirred solution of C$_3$F$_7$[OCF(CF$_3$)CF$_2$]$_2$C$_6$H$_4$OH (2.5 g, 4.2 mmol) and C$_6$H$_5$OP(O)Cl$_2$ (0.59 g, 2.8 mmol) in Freon 113 (10 mL) was added triethylamine (0.85 g, 8.4 mmol) in benzene (5 mL). The solution was then heated at 65° C. for 22 hours. Following the isolation procedure described in Example III 1.4 g of product was obtained; BP 157°–172° C./0.001 mm Hg. Under the CREP Test (Corrosion Resistance Evaluation Procedure: water vapor/100° C./1 hour/mild steel strips), the mild steel strips treated with perfluoropolyalkylether fluids such as Krytox 143AC (Du Pont trade name), Fomblin Z25 (Montedison trade name), Demnum S-100 (Daikin Industries trade name) formulated with 0.5 percent by weight of the above phosphorus material exhibited complete absence of corrosion. Strips treated with the additive-free fluids were covered by corrosion over 50–75% of the surface area.

EXAMPLE VI

In a nitrogen atmosphere to a stirred solution of C$_3$F$_7$[OCF(CF$_3$)—CF$_2$]$_3$C$_6$H$_4$OH (3.5 g, 4.6 mmol) and C$_6$H$_5$OP(O)Cl$_2$ (0.65 g, 3.1 mmol) in Freon 113 (10 mL) was added triethylamine (1.0 g, 9.9 mmol) in benzene (5 mL). The solution was then heated at 65° C. for 21 hours.

Following the isolation procedure described in Example III 2.5 g of product was obtained; BP 170°–190° C./0.001 mm Hg. Under the CREP Test (Corrosion Resistance Evaluation Procedure: water vapor/100° C./1 hour/mild steel strips), the mild steel strips treated with perfluoropolyoalkylether fluids such as Krytox 143AC (Du Pont trade name), Fomblin Z25 (Montedison trade name), Demnum S-100 (Daikin Industries trade name) formulated with 0.5 percent by weight of the above phosphorus material exhibited complete absence of corrosion. Strips treated with the additive-free fluids were covered by corrosion over 50–75% of the surface area. Using 0.5% of the phosphorus material in chlorotrifluoroethylene fluid, Halocarbon AO-2 (Halocarbon Inc. trade name) no corrosion was observed under the CREP Test. In the absence of the additive the steel strips were corroded over 40–80% of the surface area.

EXAMPLE VII

In a nitrogen atmosphere to a stirred solution of $C_3F_7(OCF(CF_3)CF_2)_2C_6H_4OH$ (8.0 g, 13.5 mmol) and $C_6H_5P(O)Cl_2$ (1.4 g, 7.0 mmol) in Freon 113 (30 mL) was added triethylamine (2.7 g, 26.9 mmol) in benzene (20 mL). The solution was then heated at 65° C. for 20 hours. Following the isolation procedure described in Example III 6.0 g (68% yield) of $[C_3F_7(OCF(CF_3)CF_2)_2 C_6H_4O]_2P(O)$—$C_6H_5$ was obtained; BP 175°–180° C./0.001 mm Hg; MW 1300 (theory 1310.46) MS (70 eV) m/e (intensity, ion): 1310 (35.6%, M), 1191 (17.6% M-$C_2F_5$), 1025 (11.4%, M-$C_3F_7OCF(CF_3)$)), 959 (18%, M-$C_3F_7OCF(CF_3)CF_2O$), 859 (82.4%, M-$C_3F_7OCF(CF_3)CF_2OCFCF_3$), 205 (21.8%, $CF_2C_6H_4OPO_2$), 143 (65.2%, $CF_2C_6H_4OH$), 69 (base, $CF_3$),

EXAMPLE VIII

In a nitrogen atmosphere to a stirred solution of $C_3F_7(OCF(CF_3)CF_2)_2C_6H_4OH$ (2.1 g, 3.6 mmol) and $(C_6H_5O)_2P(O)Cl$ (0.95 g, 3.54 mmol) in benzene (5 mL) was added triethylamine (0.78 g, 7.7 mmol) in benzene (5 mL). The solution was then heated at 85° C. for 20 hours. Following the isolation procedure described in Example III 2.8 g (95% yield) of $C_3F_7(OCF(CF_3)CF_2)_2C_6H_4OP(O)(OC_6H_5)_2$ was obtained; BP 142°–144° C./0.001 mm Hg; MW 826.38). Ms (70 eV) m/e (intensity, ion): 826 (65.4%, M), 807 (11.6%, M-F), 707 (6.3%, M-$C_2F_5$), 375 (base, $CF_2C_6H_4OPO(OC_6H_5)_2$), 233 (17.8% $PO(OC_6H_5)_2$), 189 (13.4%, $CF_2C_6H_4OPO$).

EXAMPLE IX

In a nitrogen atmosphere to a stirred solution of $C_3F_7(OCF(CF_3)CF_2)_2C_6H_4OH$ (2.0 g, 3.4 mmol) and $(C_6H_5)_2POCl$ (0.79 g, 3.3 mmol) in benzene (5 mL) was added triethylamine (0.68 g, 6.7 mmol) in benzene (5 mL). The solution was then heated at 85° C. for 21 hours. Following the isolation procedure described in Example III, after crystallization from hexane 1.8 g (67% yield) of $C_3F_7(OCF(CF_3)CF_2)_2C_6H_4OP(O)(C_6H_5)_2$ was obtained; MP 67°–70° C.; MW 830 (theory 794.38). MS (70 eV) m/e (intensity, ion): 794 (22.6%, M), 343 (11.0%, $CF_2C_6H_4OP(O)(C_6H_5)_2$), 201 (base, $PO(C_6H_5)_2$), 169 (17.1%, $C_3F_7$), 143 (13.5%, $CF_2C_6H_4OH$).

EXAMPLE X

In a nitrogen atmosphere to a stirred solution of $C_8F_{17}C_6H_4OH$ (3.0 g, 5.9 mmol) and $(C_6H_5)_2P(O)Cl$ (1.4 g, 5.8 mmol) in benzene (10 mL) was added triethylamine (1.2 g, 11.8 mmol) in benzene (10 mL). The solution was then heated at 85° C. for 24 hours. Following the isolation procedure described in Example III, after crystallization from benzene/hexane $C_8F_{17}C_6H_4OP(O)(C_6H_5)_2$ was obtained 2.6 g (63% yield); MP 110°–111° C.; MW 740 (theory 712.37). MS (70 eV) m/e (intensity, ion): 712 (32.8%, M), 693 (5.9%, M-F), 219 (14.4%, $C_4F_9$), 201 (base, $PO(C_6H_5)_2$), 143 (13.7%, $CF_2C_6H_4OH$).

EXAMPLE XI

The phosphates and phosphonates were found to effectively inhibit oxidation and volatilization of perfluoropolyalkylether fluids such as Krytox 143AC (Du Pont trade name) and Fomblin Z25 (Montedison trade name) and to prevent corrosion of M-50 steel alloy at elevated temperatures in oxygen atmospheres. This is illustrated in Table 1.

TABLE 1

Degradation of Perfluoropolyalkylether Fluids in the Presence of M-50 Alloy at 316° C. in Oxygen over 24 Hours[a] and the Additives' Effect

| Fluid Type | Additive g | 1% | Volitiles mg | mg/g[b] |
|---|---|---|---|---|
| K[c] | 12.1 | None | 577. | 47.5 |
| K | 3.26 | $[C_3F_7(OCF(CF_3)CF_2)_2C_6H_4O]_2P(O)OC_6H_5$ | 0.8 | 0.25 |
| K | 2.96 | $[C_3F_7(OCF(CF_3)CF_2)_2C_6H_4O]_2P(O)C_6H_5$ | 0.1 | 0.03 |
| K | 2.91 | $C_3F_7(OCF(CF_3)CF_2)_2C_6H_4OP(O)(OC_6H_5)_2$ | 0.6 | 0.21 |
| K | 3.11 | $C_3F_7(OCF(CF_3)CF_2)_2C_6H_4OP(O)(C_6H_5)_2$ | 0.8 | 0.26 |
| K | 3.33 | $C_8F_{17}C_6H_4OP(O)(C_6H_5)_2$ | 0.8 | 0.24 |
| K | 3.04 | $[C_3F_7(OCF(CF_3)CF_2)_3C_6H_4O]_2P(O)OC_6H_5$ | 0.2 | 0.07 |
| F[d] | 3.09 | None (exposure 8 hours)[e] | 1042. | 337. |
| F | 3.02 | $C_2F_5C_6H_4OP(O)(OC_6H_5)_2$ | 2.2 | 0.73 |
| F | 3.10 | $C_3F_7(OCF(CF_3)CF_2)_2C_6H_4OP(O)(OC_6H_5)_2$ | 0.8 | 0.26 |
| F | 3.14 | $C_8F_{17}C_6H_4OP(O)(C_6H_5)_2$ | 1.6 | 0.51 |
| F | 3.21 | $C_3F_7(OCF(CF_3)CF_2)_4C_6H_4OP(O)(OC_6H_5)_2$ | 3.9 | 1.2 |
| F | 3.26 | $C_3F_7(OCF(CF_3)CF_2)_3C_6H_4O]_2P(O)OC_6H_5$ | 0.8 | 0.24 |

TABLE 1-continued

Degradation of Perfluoropolyalkylether Fluids in the Presence of M-50 Alloy at 316° C. in Oxygen over 24 Hours[a] and the Additives' Effect

| Fluid Type | Additive g 1% | Volitiles mg | mg/g[b] |
|---|---|---|---|

[a] The apparatus consisted of a sealed glass tube wherein the metal coupon was suspended in the fluid; the test was conducted in pure oxygen; at the conclusion of the test, the volatile products formed were collected and measured.
[b] Products formed in mg per g of perfluoropolyalkylether fluid employed.
[c] K denotes Krytox 143AC fluid.
[d] F denotes Fomblin Z25 fluid.
[e] In the absence of additive total volatilization occurred during a 24 hour exposure.

INDUSTRIAL APPLICATION

The invention has application in the chemical process industries and in the manufacture of additives for perfluoropolyalkylether based lubricants. The use of the additives, herein disclosed, provides for rust protection, lubricity enhancement and the corrosion/degradation inhibition permitting utilization of the perfluoropolyalkylether lubricants at elevated temperatures or under boundary lubrication conditions in the presence of metals/metal alloys in oxidizing atmospheres for extended periods of time.

What is claimed is:

1. Phosphates of the general formula $(R_fC_6H_4O)_xP(O)(OR)_{3-x}$; wherein:

x is an integer 1, 2, or 3; and $R_f$ is selected from the group consisting of:

(a) substituents having a general formula $C_nF_{2n+1}$, wherein n is an integer from 2 to 10 inclusive;

(b) $C_3F_7(OCF(CF_3)CF_2)_m$, (c) $CF_3(OCF_2CF_2)_m$, (d) $C_2F_5(OCF_2CF_2)_m$, (e) $C_3F_7(OCF_2CF_2CF_2)_m$, and (f) $C_4F_9(OCF_2CF_2CF_2CF_2)_m$, wherein m is an integer from 1 to 20 inclusive, and R is $C_6H_5$ or $R'C_6H_4$, wherein R' is phenyl, alkyl, $SC_6H_5$ or $OC_6H_5$.

2. A composition of matter comprising a phosphate of having the general formula $(C_8F_{17}C_6H_4O)_2P(O)OC_6H_5$, $C_8F_{17}C_6H_4OP(O)(OC_6H_5)_2$, $[C_3F_7(OCF(CF_3)CF_2)_nC_6H_4]_2P(O)OC_6H_5$ or $C_3F_7(OCF(CF_3)CF_2)_nC_6H_4OP(O)(OC_6H_5)_2$ wherein n=2, 3, 4.

3. A mixture of compounds comprising:

(a) $(R_fC_6H_4O)_xP(O)(OR)_{2-x}(OH)$ wherein x is an integer 1 or 2, $R_f$ is selected from (i) groups having a general formula $C_nF_{2n+1}$, wherein n is an integer from 2 to 10 inclusive;

(ii) $C_3F_7(OCF(CF_3)CF_2)_m$, (iii) $CF_3(OCF_2CF_2)_m$, (iv) $C_2F_5(OCF_2CF_2)_m$, (v) $C_3F_7(OCF_2CF_2CF_2)_m$, and (vi) $C_4F_9(OCF_2CF_2CF_2CF_2)_m$ wherein m is an integer from 1 to 20 inclusive, and R is selected from $C_6H_5$ or $R'C_6H_4$, wherein R' is phenyl, alkyl, $SC_6H_5$ or $OC_6H_5$; and (b) $(R_fC_6H_4O)_xP(O)(OR)_{3-x}$ wherein x is an integer 1, 2, or 3, $R_f$ is selected from (i) groups having a general formula $C_nF_{2n+1}$, wherein n is an integer from 2 to 10 inclusive;

(ii) $C_3F_7(OCF(CF_3)CF_2)_m$, (iii) $CF_3(OCF_2CF_2)_m$, (iv) $C_2F_5(OCF_2CF_2)_m$, (v) $C_3F_7(OCF_2CF_2CF_2)_m$, and (vi) $C_4F_9(OCF_2CF_2CF_2CF_2)_m$ wherein m is an integer from 1 to 20 inclusive, and R is selected from $C_6H_5$ or $R'C_6H_4$, wherein R' is phenyl, alkyl, $SC_6H_5$ or $OC_6H_5$.

4. A composition as claimed in claim 3 comprising a mixture of from 2% to 90% of $(C_8F_{17}C_6H_4O)P(O)(OH)(OC_6H_5)$ and 98% to 10% of $(C_8F_{17}C_6H_4O)_2P(O)(OC_6H_5)$.

5. A composition as claimed in claim 3 comprising a mixture of 2% to 90% of $(C_3F_7(OCF(CF_3)CF_2)_2C_6H_4O)P(O)(OH)(OC_6H_5)$ and 98% to 10% of $(C_3F_7(OCF(CF_3)CF_2)_2C_6H_4O)_2P(O)(OC_6H_5)$.

6. A composition as claimed in claim 3 comprising a mixture of 2% to 90% of $(C_3F_7(OCF(CF_3)CF_2)C_6H_4O)P(O)(OH)(OC_6H_5)$ and 98% to 10% of $(C_3F_7(OCF(CF_3)CF_2)_3C_6H_4O)_2P(O)(OC_6H_5)$.

7. A composition comprising one or more phosphonates of the general formula $(R_fC_6H_4O)_2P(O)R$ wherein $R_f$ is selected from the group consisting of:

(i) compounds having a general formula $C_nF_{2n+1}$, wherein n is an integer from 2 to 10 inclusive, (ii) $C_3F_7(OCF(CF_3)CF_2)_m$, (ii) $CF_3(OCF_2CF_2)_m$, (iii) $C_2F_5(OCF_2CF_2)_m$, (iv) $C_3F_7(OCF_2CF_2CF_2)_m$, and (v) $C_4F_9(OCF_2CF_2CF_2CF_2)_m$ wherein m is an integer from 1 to 20 inclusive and wherein R groups include $C_6H_5$ and $R'C_6H_4$, where R' is phenyl, alkyl, $SC_6H_5$ or $OC_6H_5$.

8. A composition in accordance with claim 7 wherein the phosphonate is selected from the group consisting of $(C_8F_{17}C_6H_4O)_2P(O)C_6H_5$, and $C_3F_7(OCF(CF_3)CF_2)_nC_6H_4O]_2P(O)C_6H_5$ wherein n=2, 3, or 4.

9. A composition of matter comprising a mixture of at least one compound of the formula $(R_fC_6H_4O)P(O)R(OH)$ and at least one compound of the formula $(R_fC_6H_4O)_2P(O)R$ wherein R is selected from the group consisting of $C_6H_5$, and $R'C_6H_4$, wherein R' is phenyl, alkyl, $SC_6H_5$ or $OC_6H_5$ and wherein $R_f$ is selected from the group consisting of:

(a) substituents having a general formula $C_nF_{2n+1}$, wherein n is an integer from 2 to 10 inclusive, (b) $C_3F_7(OCF(CF_3)CF_2)_m$, (c) $CF_3(OCF_2CF_2)_m$, (d) $C_2F_5(OCF_2CF_2)_m$, (e) $C_3F_7(OCF_2CF_2CF_2)_m$ and (d) $C_4F_9(OCF_2CF_2CF_2CF_2)_m$ wherein m is an integer from 1 to 20 inclusive.

10. A composition of matter comprising one or more phosphonates of the general formula $(R_fC_6H_4O)P(O)R_2$ wherein $R_f$ is selected from the group consisting of:

(a) $C_3F_7(OCF(CF_3)CF_2)_m$, (b) $CF_3(OCF_2CF_2)_m$, (c) $C_2F_5(OCF_2CF_2)_m$, (d) $C_3F_7(OCF_2CF_2CF_2)_m$, and (e) $C_4F_9(OCF_2CF_2CF_2CF_2)_m$ wherein m is an integer from 1 to 20 inclusive and wherein R groups are selected from $C_6H_5$ and $R'C_6H_4$, where R' is phenyl, alkyl, $SC_6H_5$ or $OC_6H_5$.

11. A composition in accordance with claim 10 wherein the phosphonate is $C_3F_7(OCF(CF_3)CF_2)_nC_6H_4OP(O)(C_6H_5)_2$ wherein n=2, 3 or 4.

* * * * *